United States Patent
Li et al.

(10) Patent No.: US 9,293,313 B2
(45) Date of Patent: Mar. 22, 2016

(54) SPATIAL FOCUSING ION GATE ASSEMBLY AND SPATIAL FOCUSING ION MOBILITY SPECTROMETER

(75) Inventors: Haiyang Li, Liaoning (CN); Yongzhai Du, Liaoning (CN); Weiguo Wang, Liaoning (CN)

(73) Assignee: DALIAN INSTITUTE OF CHEMICAL PHYSICS, CHINESE ACADEMY OF SCIENCES, Dalian, Liaoning (CN)

( * ) Notice: Subject to any disclaimer, the term of this patent is extended or adjusted under 35 U.S.C. 154(b) by 0 days.

(21) Appl. No.: 14/119,508

(22) PCT Filed: Nov. 18, 2011

(86) PCT No.: PCT/CN2011/082451
§ 371 (c)(1),
(2), (4) Date: Nov. 22, 2013

(87) PCT Pub. No.: WO2013/020336
PCT Pub. Date: Feb. 14, 2013

(65) Prior Publication Data
US 2014/0084155 A1 Mar. 27, 2014

(30) Foreign Application Priority Data
Aug. 9, 2011 (CN) .......................... 2011 1 0226912

(51) Int. Cl.
*G01N 27/62* (2006.01)
*H01J 49/06* (2006.01)
*H01J 49/26* (2006.01)
(52) U.S. Cl.
CPC ............ *H01J 49/061* (2013.01); *G01N 27/622* (2013.01)

(58) Field of Classification Search
CPC .............................. H01J 49/061; G01N 27/622
USPC .................................................. 250/281–300
See application file for complete search history.

(56) References Cited

U.S. PATENT DOCUMENTS

| 6,459,079 | B1 * | 10/2002 | Machlinski et al. | 250/286 |
| 2005/0205775 | A1 | 9/2005 | Bromberg et al. | |
| 2006/0231751 | A1 * | 10/2006 | Zuleta | H01J 49/0018 250/287 |
| 2008/0179515 | A1 * | 7/2008 | Sperline | 250/290 |
| 2010/0224776 | A1 | 9/2010 | Wu | |
| 2010/0230588 | A1 * | 9/2010 | Atkinson et al. | 250/283 |
| 2012/0199735 | A1 * | 8/2012 | Krechmer et al. | 250/286 |

FOREIGN PATENT DOCUMENTS

| CN | 101562114 A | 10/2009 |
| CN | 201378582 Y | 1/2010 |
| CN | 101750264 A | 6/2010 |

* cited by examiner

*Primary Examiner* — Robert Kim
*Assistant Examiner* — Eliza Osenbaugh-Stewart
(74) *Attorney, Agent, or Firm* — Novick, Kim & Lee, PLLC; Allen Xue

(57) ABSTRACT

Provided is a spatial focusing ion mobility tube, including an ionization source, an ion gate, a grid mesh and a faraday disc. A focusing grid mesh parallel to the ion gate is provided at one side of the ion gate away from the ionization source, and the ion gate and the focusing grid mesh combine into a spatial focusing ion gate assembly which controls the flight of the ions. The mobility tube employs a traditional design and changes the ion gate portion to one or more spatial focusing ion gate assemblies. The spatial focusing assembly can realize the injection function of the ion gate and produce the spatial compression focusing of ions.

13 Claims, 2 Drawing Sheets

SPATIAL FOCUSING ION GATE ASSEMBLY AND SPATIAL FOCUSING ION MOBILITY SPECTROMETER

FIELD OF THE INVENTION

This invention relates to the field of drift tube ion mobility spectrometer, specifically a spatial focusing ion mobility spectrometer. The spatial focusing of ions is achieved via a specific design of ion gate leading to the spatial focusing of the ion cloud and the evident increase of resolution and sensitivity of ion mobility spectrometer. Provided is an technique in the field of instrument analysis.

BACKGROUND OF THE INVENTION

Spatial focusing of ions was used in field of mass spectrometry, which avoids the difference of flight time for the same ions with different velocity due to their initial different position and potential. Evident increase of resolution of mass spectrometry was achieved with the use of spatial focusing technique.

The focusing of ion in mass spectrometry was realized in vacuum where ions fly under the actions of acceleration of electrical field and inertia. Thus, the energy loss of ions could be negligible due to the low possibility of collisions with other particles. However, ion mobility spectrometry separates the different ions at atmospheric pressure. The electric field was used to overcome the obstruction due to the collision of ions with molecules of drift gas. To realize the focusing of ions at atmospheric pressure, a non-uniform electric field ($\partial E/\partial d \neq 0$) is essential in initial conditions, which makes the lagged ions obtain higher velocity and pursue the front ions at the beginning. Thus, the focusing of ion was realized.

The spatial focusing of ion under atmospheric pressure was realized in high-field asymmetric waveform ion mobility spectrometry, which separate different ions based on the different mobility between high-field portion and low-field portion of the waveform. Spatial focusing is achieved in high-field asymmetric waveform ion mobility spectrometry with cylindrical structure based on the amplitude variation of drift length of ions in radial positions in the separation space.

As far as we know, there is no report about the focusing linear drift tube ion mobility spectrometry. For the first time this invention introduced the linear drift tube ion mobility spectrometry with the function of focusing. The spatial focusing of ions is achieved using a non-uniform electric field based a simple structure and was verified with experimental results.

SUMMARY OF THE INVENTION

This invention provides a simple construction spatial focusing ion gate assembly with spatial focusing function and also spatial focusing ion mobility spectrometer.

To realize this purpose, the technical proposal is presented as follows:

The spatial focusing ion gate assembly is composed with an ion gate and a focusing grid. The conventional structure is deployed in which one or more spatial focusing ion gate assembly or assemblies substituting for the conventional ion gate. And the injection function of the ion gate and also the spatial compression focusing function realized with the use of spatial focusing ion gate assembly.

More details:

A spatial focusing ion gate assembly including ion gate, wherein a focusing grid locates on the side of ion gate and parallels to ion gate and the spatial focusing ion gate assembly is composed with an ion gate and a focusing grid. Ion gate could be the Bradbury-Nielsen gate or Tyndall-Powell gate.

The distance from the ion gate to focusing grid in spatial focusing ion gate assembly is in the range of 0.1 mm to 10 cm.

A spatial focusing ion mobility spectrometer comprising ionization source, ion gate, grid, faraday plate. Focusing grid locates on the side of ion gate in the far away from ionization source and parallels to ion gate. The spatial focusing ion gate assembly composed with ion gate and focusing grid is used to control the flights of ions.

There is one spatial focusing ion gate assembly, dividing drift tube into two regions: the reaction region between ionization source and focusing grid and the drift region between focusing grid and faraday plate.

There are more than two spatial focusing ion gate assemblies which are parallel to each other. The spatial focusing ion gate assembly near the ionization source divides the drift tube into two regions: the reaction region between ionization source and focusing grid and the drift region between focusing grid and faraday plate; other spatial focusing ion gate assemblies locate in the drift region.

The distance from the ion gate to the focusing grid which are parallel to each other is in the range of 0.1 mm to 10 cm.

The ion gate is the Bradbury-Nielsen gate, which is composed with two groups of insulation metal wires placed parallel and coplanar. One group of metal wires was fixed at a constant electrical voltage equal to that in the same position of drift tube, other group of wires is applied a periodic voltage with value higher than that fixed value in the first group of wires 100% to 300%. The different voltage between those two groups of wires produces an electrical field to control the movement of ions and realized the function of ion gate to inject the ions into the drift region; a constant voltage is applied to the focusing grid with absolute value lower than that on the first group of wires and the value is bigger than 0 and smaller than 200% of the potential value in the position of drift tube; the voltage on the second group of metal wires and the focusing grid forms an electrical field with function of focusing and compress the injected ions.

The ion gate is the Tyndall-Powell gate, which is composed with two groups of metal wires or grids. The wires in the same group are placed parallel in planes offset by a small distance. One grid is fixed at a constant electrical voltage equal to that in the same position of drift tube, the other grid is applied a periodic voltage with value higher than that fixed value in the first grid 100% to 300%. The voltage difference between those two grids produces an electrical field to control the movement of ions and realized the function of ion gate to inject the ions into the drift region; a constant voltage is applied to the focusing grid with absolute value lower than that on the first grid and the value is = bigger than 0 and smaller than 200% of the potential value in the position of drift tube; the voltage on the second grid and the focusing grid forms an electrical field with function of focusing and compress the injected ions.

1—spatial focusing ion gate assembly; 2—ion gate; 3—grid; 4—ionization source; 5—reaction region; 6—drift region; 7—grid and faraday plate.

Figure 3:
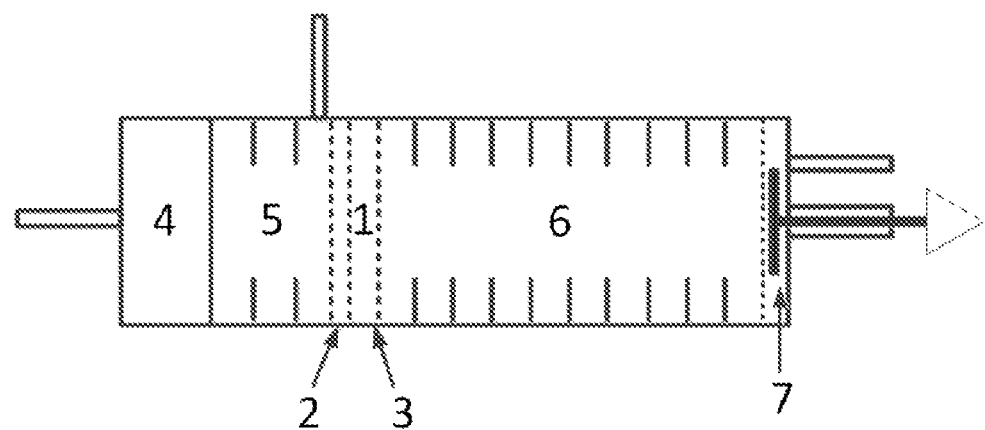

FIG. 3 shows a spatial focusing drift tube ion mobility spectrometry with Tyndall-Powell ion gate. Inside: 1—spatial focusing ion gate assembly; 2—ion gate; 3—grid; 4—ionization source; 5—reaction region; 6—drift region; 7—grid and faraday plate.

Figure 4:
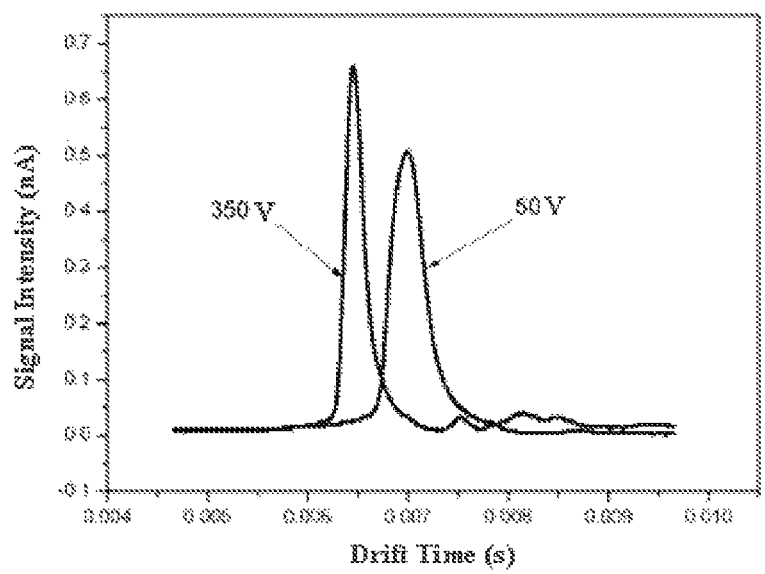

FIG. 4 shows the spectrum of ion mobility spectrometry.

DETAILED DESCRIPTION OF THE PREFERRED EMBODIMENT

Example 1

Figure 1:
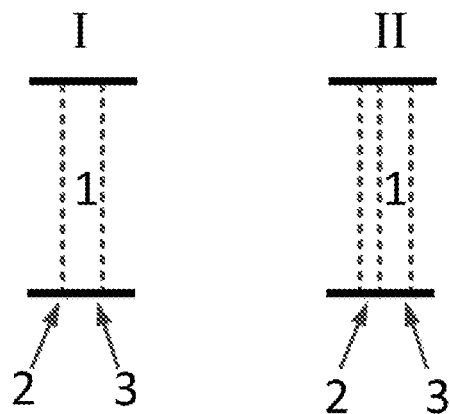
FIG. 1 shows the schematic diagram of a spatial focusing ion gate assembly: 1—spatial focusing ion gate assembly; 2—ion gate; 3—grid; (I) with Bradbury-Nielsen ion gate structure; (II) with Tyndall-Powell ion gate structure.

As shown in FIG. 1, a spatial focusing ion gate assembly comprising a ion gate, focusing grid (3) located on the side of ion gate (2) and parallel to ion gate (2). Said ion gate (2) and focusing grid (3) make up the spatial focusing ion gate assembly (1).

Said ion gate is the Bradbury-Nielsen gate or Tyndall-Powell gate; in spatial focusing ion gate assembly (1), the distance from the ion gate to the focusing grid is in the range of 2 mm to 1 cm.

Example 2

Figure 2:
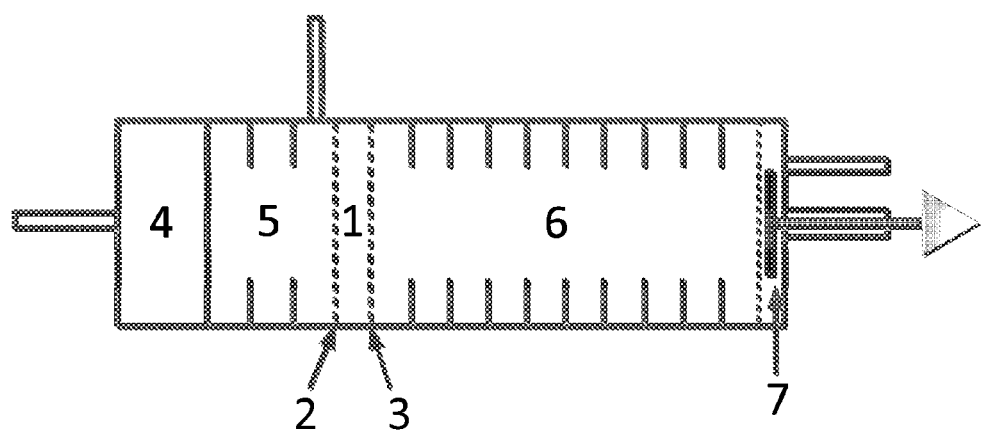
FIG. 2 shows a spatial focusing drift tube ion mobility spectrometry with Bradbury-Nielsen ion gate. Inside.

As shown in FIG. 2, A spatial focusing drift tube ion mobility spectrometer comprising: ionization source, ion gate, grid and faraday plate. Focusing grid (3) locates on the side of ion gate (2) far away from ionization source and parallels to ion gate (2). The spatial focusing ion gate assembly (1) composed with the said ion gate (2) and focusing grid (3) was used to control the flight of ions.

There is one spatial focusing ion gate assembly, dividing drift tube into two regions: the reaction region between ionization source and focusing grid and the drift region between focusing grid and faraday plate.

There are more than one spatial focusing ion gate assemblies which are parallel to each other, the spatial focusing ion gate assembly near the ionization source divides the drift tube into two regions: the reaction region between ionization source and focusing grid and the drift region between focusing grid and faraday plate; other spatial focusing ion gate assemblies (1) locate in the drift region.

Said drift tube ion mobility spectrometer, wherein the distance from the ion gate and focusing grid is in the range of 0.1 mm to 2 cm.

Said ion gate (2) is the Bradbury-Nielsen gate, which is composed with two groups of metal wires placed parallel and coplanar at close separations. One group of metal wires was fixed at a constant electrical voltage equal to that in the same position of drift tube, other group of wires is applied a periodic voltage with value higher than that fixed value in the first group of wires 100% to 300%. The different voltage between those two groups of wires produces an electrical field to control the movement of ions and realized the function of ion gate to inject the ions into the drift region (6); a constant voltage is applied to the focusing grid with absolute value lower than that on the first group of wires and the value is bigger than 0 and smaller than 200% of the potential value in the position of drift tube; the voltage on the second group of metal wires and the focusing grid forms an electrical field with function of focusing and compress the injected ions.

Example 3

As shown in FIG. 3, a spatial focusing drift tube ion mobility spectrometer comprising: ionization source, ion gate, grid and faraday plate. Focusing grid locates on the side of ion gate (2) far away from ionization source and parallels to ion gate (2). The spatial focusing ion gate assembly (1) was composed with the said ion gate (2) and focusing grid (3).

There is one spatial focusing ion gate assembly, dividing drift tube into two regions: the reaction region between ionization source and focusing grid, and the drift region between focusing grid and faraday plate.

There are more than two spatial focusing ion gate assemblies which are parallel each other, the spatial focusing ion gate assembly near the ionization source divides the drift tube into two regions: the reaction region between ionization source and focusing grid and the drift region between focusing grid and faraday plate; other spatial focusing ion gate assemblies locate in the drift region.

Said drift tube ion mobility spectrometer, wherein the distance from the ion gate (2) and focusing grid (3) is in the range of 2 mm to 1 cm.

Said ion gate (2) is the Tyndall-Powell ion gate, which is composed with two groups of metal wires or grid. The wires or grids in the same group are placed parallel in planes offset by a small distance. One grid was fixed at a constant electrical voltage equal to that in the same position of drift tube, other grid is applied a periodic voltage with value higher than that fixed value in the first grid 100% to 300%. The different voltage between those two grids produces an electrical field to control the movement of ions and realized the function of ion gate to inject the ions into the drift region (6); a constant voltage is applied to the focusing grid with absolute value lower than that on the first grid and the value is bigger than 0 and smaller than 200% of the potential value in the position of drift tube; the voltage on the second grid and the focusing grid forms an electrical field with function of focusing and compress the injected ions.

Example for Application

A drift tube ion mobility spectrometer with spatial focusing assembly Bradbury-Nielsen ion gate is introduced. The drift length is 6.25 cm, the electric strength is 240 V/cm, the fixed electric voltage difference between ion gate and the focusing grid is 72 V, the temperature of the drift tube is 100° C., the flow rate of drift gas and carrier gas are both 500 SCCM, 60 ppm dichloromethane was used as the sample. The spatial focusing assembly Bradbury-Nielsen ion gate shown in FIG. 1 was used and the distance from ion gate to the grid is 5 mm. The voltage values between the first and second groups of metal wires are 50 V and 350 V respectively and the pulse width of the ion gate is 340 us. The experimental result was shown in FIG. 4.

For voltage difference of 50 V, the full width at half maximum and signal intensity of the peak is 0.39 ms and 0.508 nA; however, for voltage difference of 350 V, the full width at half maximum and signal intensity of the peak is only 0.21 ms and 0.66 nA.

What is claimed is:
1. An ion mobility tube, comprising:
a spatial focusing ion gate assembly;
an ionization source; and
a faraday plate,
wherein the spatial focusing ion gate assembly comprises an ion gate and a focusing grid, wherein the focusing grid is adjacent to and parallel to the ion gate,
wherein the spatial focusing ion gate assembly is disposed in the ion mobility tube between the ionization source and the faraday plate so that a drift region of the ion mobility tube is located between the focusing grid and the faraday plate, and wherein the ion gate is a Bradbury-Nielsen ion gate.

2. The ion mobility tube according to claim 1, wherein the focusing grid is coupled to a constant voltage source.

3. An ion mobility spectrometer, comprising:
an ionization source, a Bradbury-Nielsen ion gate, a focusing grid, and a faraday plate,
wherein the ionization source, the Bradbury-Nielsen ion gate, the focusing grid, and the faraday plate are sequentially arranged so that the focusing grid is disposed on the side of the ion gate away from the ionization source and is between the Bradbury-Nielsen ion gate and the faraday plate; and
a constant voltage source coupled to the focusing grid.

4. The ion mobility spectrometer according to claim 3, wherein a distance between the Bradbury-Nielsen ion gate and the focusing grid is in a range of 0.1 mm to 2 cm.

5. The ion mobility spectrometer according to claim 3, wherein the Bradbury-Nielsen ion gate comprises a first group of metal wires and a second group of metal wires placed coplanar with each other, the first group of metal wires is at a first constant voltage and the second group of metal wires is at a periodic voltage.

6. The ion mobility spectrometer according to claim 3, wherein the periodic voltage varies from one time to three times of the first constant voltage.

7. The ion mobility spectrometer according to claim 3, wherein the focusing grid is at a constant voltage that is lower than the first constant voltage.

8. The ion mobility spectrometer according to claim 3, further comprising one or more additional focusing grids disposed between the focusing grid and the faraday plate.

9. A method of compressing an ion pulse in an ion mobility spectrometer, wherein the ion mobility tube comprises an ionization source, a Bradbury-Nielsen ion gate, a focusing grid, and a faraday plate, wherein the ionization source, the Bradbury-Nielsen ion gate, the focusing grid, and the faraday plate are sequentially arranged so that the focusing grid is disposed on the side of the ion gate away from the ionization source and is between the Bradbury-Nielsen ion gate and the faraday plate;
the method comprising the step of:
applying a first constant voltage to a first group of wires in the Bradbury-Nielsen ion gate;
applying a periodic voltage to a second group of wires in the Bradbury-Nielsen ion gate, wherein the periodic voltage varies from one time to three times the first constant voltage; and
applying a second constant voltage to the focusing grid so that a potential of the focusing grid is larger than zero volt and smaller than two times a potential at the location in the ion mobility tube where the focusing grid is located, wherein the second constant voltage is lower than the first constant voltage.

10. The method of claim 9, wherein the first constant voltage is applied so that a potential of the first group of wires in the Bradbury-Nielsen ion gate equals to a potential in the ion mobility tube where the Bradbury-Nielsen ion gate is located.

11. The method of claim 9, wherein the focusing grid is parallel to the ion gate, wherein a distance between the focusing grid and the ion gate is in a range of 0.1 mm to 2 cm.

12. The method of claim 11, wherein the distance between the focusing grid and the ion gate is in a range of 2 mm to 1 cm.

13. The method of claim 9, wherein the second constant voltage is applied so that a potential of the focusing grid equals to a potential in the ion mobility tube where the Bradbury-Nielsen ion gate is located.

* * * * *